(12) United States Patent
Kolczewski et al.

(10) Patent No.: US 8,143,273 B2
(45) Date of Patent: Mar. 27, 2012

(54) QUINOLIZIDINE AND INDOLIZIDINE DERIVATIVES

(75) Inventors: Sabine Kolczewski, Loerrach (DE); Emmanuel Pinard, Linsdorf (FR)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 13/161,534

(22) Filed: Jun. 16, 2011

(65) Prior Publication Data

US 2011/0313165 A1    Dec. 22, 2011

(30) Foreign Application Priority Data

Jun. 22, 2010    (EP) ..................... 10166776

(51) Int. Cl.
*A61K 31/44* (2006.01)
*C07D 217/02* (2006.01)
(52) U.S. Cl. ...................... 514/306; 546/144
(58) Field of Classification Search ............... 514/306; 546/144
See application file for complete search history.

(56) References Cited

U.S. PATENT DOCUMENTS

2009/0258899 A1    10/2009    Dargazanli et al.

FOREIGN PATENT DOCUMENTS

| EP | 0044573 | 1/1982 |
| FR | 2906251 | 3/2008 |
| WO | 02/24695 | 3/2002 |
| WO | WO 2009153721 | * 12/2009 |

OTHER PUBLICATIONS

Gainetdinov et al., "Trends in Pharm. Sci." 23(8):367-373 ( 2002).
Mohn et al., "Cell" 98:427-436 ( 1999).
Tang et al., "Nature" 401:63-69 ( 1999).
Nakazato et al., "Exp. Opin. Ther. Patents" 10(1):75-98 ( 2000).
Pralong et al., "Prog. Neurobiol." 67:173-202 ( 2002).
PCT International Search Report mailed Sep. 21, 2011—PCT/EP2011/060077.
Bergereon et al., "Proc. Natl. Acad. Sci. USA" 95:15730-15734 ( 1998).
Sharma et al., "J. Psychiatry" 174:44-51 ( 1999).
Javitt et al., "Biol. Psychiatry" 45:668-679 ( 1999).
Bliss et al., "Nature" 361:31-39 ( 1993).
Carlsson, M. L., "J.Neural Transm." 105:525-535 ( 1998).
Lewis et al., "Neuron" 28:325-333 ( 2000).
Armer et al., "Exp. Opin. Ther. Patents" 11(4):563-572 ( 2001).
Vandenberg et al., "Exp. Opinion Ther. Targets" 5(4):507-518 ( 2001).
Chen et al., "Neurophysiol." 89(2):691-703 ( 2003).

* cited by examiner

*Primary Examiner* — Binta Robinson
(74) *Attorney, Agent, or Firm* — George W. Johnston; Patricia S. Rocha-Tramaloni; Kimberly J. Prior

(57) ABSTRACT

The present invention relates to a compound of formula I-A or I-B

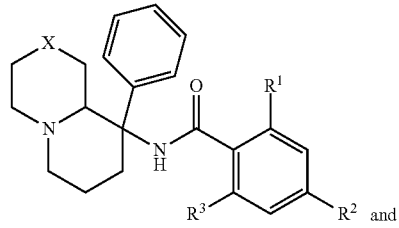

I-A

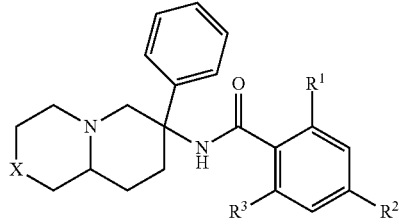

I-B wherein X,
$R^1$, $R^2$ and $R^3$ are defined herein; or to a pharmaceutically acceptable acid addition salt, to a racemic mixture, or to its corresponding enantiomer and/or optical isomer thereof. The compounds of formulas I-A and I-B are good inhibitors of the glycine transporter 1 (GlyT-1), and have a good selectivity to glycine transporter 2 (GlyT-2) inhibitors, suitable in the treatment of neurological and neuropsychiatric disorders.

10 Claims, No Drawings

QUINOLIZIDINE AND INDOLIZIDINE DERIVATIVES

PRIORITY TO RELATED APPLICATION(S)

This application claims the benefit of European Patent Application No. 10166776.4, filed Jun. 22, 2010, which is hereby incorporated by reference in its entirety.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 2000, 28:325-33). For decades research has focused on the "dopaminergic hyperactivity" hypothesis which has led to therapeutic interventions involving blockade of the dopaminergic system (Vandenberg R J and Aubrey K R., Exp. Opin. Ther. Targets, 2001, 5(4): 507-518; Nakazato A and Okuyama S, et al., 2000, Exp. Opin. Ther. Patents, 10(1): 75-98). This pharmacological approach poorly address negative and cognitive symptoms which are the best predictors of functional outcome (Sharma T., Br. J. Psychiatry, 1999, 174(suppl. 28): 44-51).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., 1999, Biol. Psychiatry, 45: 668-679 and refs. herein). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., 1999, Cell, 98: 427-236).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Hebb D O, 1949, The organization of behavior, Wiley, NY; Bliss T V and Collingridge G L, 1993, Nature, 361: 31-39). Transgenic mice over-expressing the NMDA NR2B subunit exhibit enhanced synaptic plasticity and superior ability in learning and memory (Tang J P et al., 1999, Nature: 401-63-69).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, 2002, Trends in Pharm. Sci., 23(8): 367-373).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., 2001, Mol. Mem. Biol., 18: 13-20). Thus, one strategy to enhance NMDA receptor activity is to elevate the glycine concentration in the local microenvironment of synaptic NMDA receptors by inhibition of GlyT-1 transporter (Bergereon R. Et al., 1998, Proc. Natl. Acad. Sci. USA, 95: 15730-15734; Chen L et al., 2003, J. Neurophysiol., 89 (2): 691-703).

Glycine transporters inhibitors are suitable for the treatment of neurological and neuropsychiatric disorders. The majority of diseases states implicated are psychoses, schizophrenia (Armer R E and Miller D J, 2001, Exp. Opin. Ther. Patents, 11 (4): 563-572), psychotic mood disorders such as severe major depressive disorder, mood disorders associated with psychotic disorders such as acute mania or depression associated with bipolar disorders and mood disorders associated with schizophrenia, (Pralong E T et al., 2002, Prog. Neurobiol., 67: 173-202), autistic disorders (Carlsson M L, 1998, J. Neural Transm. 105: 525-535), cognitive disorders such as dementias, including age related dementia and senile dementia of the Alzheimer type, memory disorders in a mammal, including a human, attention deficit disorders and pain (Armer R E and Miller D J, 2001, Exp. Opin. Ther. Patents, 11 (4): 563-572).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

The present invention provides a compound of formula I-A or I-B

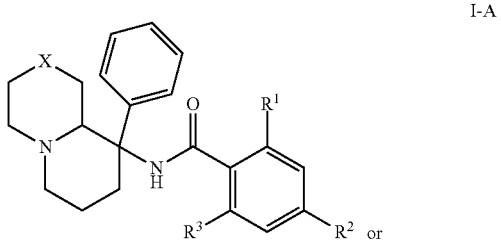

I-A

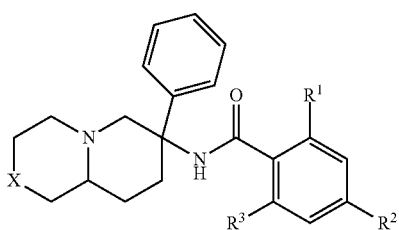

wherein

X is a bond or a —CH$_2$— group;

R$^1$, R$^2$ and R$^3$ are each independently hydrogen, lower alkoxy, lower alkyl substituted by halogen or S-lower alkyl;

or a pharmaceutically acceptable acid addition salt, a racemic mixture, or a corresponding enantiomer and/or optical isomer thereof.

Furthermore, the present invention provides pharmaceutical compositions containing the compounds of formulas I-A and I-B and to their use in the treatment of neurological and neuropsychiatric disorders.

The compounds of formulas I-A and I-B are good inhibitors of the glycine transporter 1 (GlyT-1) and have a good selectivity to glycine transporter 2 (GlyT-2) inhibitors.

The present invention provides the compounds of formulas I-A and I-B per se and pharmaceutical compositions containing them. The invention also provides methods for the manufacture of the compounds and compositions of the invention. The invention further provides the use of compounds of formulas I-A and I-B and their pharmaceutically acceptable salts for the treatment of diseases related to activation of NMDA receptors via Glyt-1 inhibition. The invention also provides methods for the use of compounds of formulas I-A and I-B in the control or prevention of illnesses such as psychoses, dysfunction in memory and learning, schizophrenia, dementia and other diseases in which cognitive processes are impaired, such as attention deficit disorders or Alzheimer's disease.

The present invention further provides a method for the treatment or prophylaxis of psychoses, pain, dysfunction in memory and learning, attention deficit, schizophrenia, dementia disorders or Alzheimer's disease, which method comprises administering an effective amount of a compound. of formula I-A or I-B to a mammal in need.

The preferred indications using the compounds of the present invention are schizophrenia, cognitive impairment and Alzheimer's disease.

Furthermore, the invention includes all racemic mixtures, all their corresponding enantiomers and/or optical isomers.

DETAILED DESCRIPTION OF THE INVENTION

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a lower alkyl group as defined above, which is attached via an O atom.

The term "halogen" denotes chlorine, iodine, fluorine and bromine.

The term "lower alkyl substituted by halogen" denotes a lower alkyl group as defined above, wherein at least one hydrogen atom is replaced by a halogen atom, for example the following groups: CF$_3$, CHF$_2$, CH$_2$F, CH$_2$CF$_3$, CH$_2$CHF$_2$, CH$_2$CH$_2$F, CH$_2$CH$_2$CF$_3$, CH$_2$CH$_2$CH$_2$CF$_3$, CH$_2$CH$_2$Cl, CH$_2$CF$_2$CF$_3$, CH$_2$CF$_2$CHF$_2$, CF$_2$CHFCF$_3$, C(CH$_3$)$_2$CF$_3$, CH(CH$_3$)CF$_3$ or CH(CH$_2$F)CH$_2$F. The preferred "lower alkyl substituted by halogen" group is CF$_3$.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

One embodiment of the invention provides compounds of formula I-A, wherein X is CH$_2$, for example 2-methoxy-6-methylsulfanyl-N-((1S,R; 9aR,S)-1-phenyl-octahydro-quinolizin-1-yl)-4-trifluoromethyl-benzamide.

A further embodiment of the invention provides compounds of formula I-A, wherein X is a bond, for example 2-methoxy-6-methylsulfanyl-N-((8S,R; 8aR,S)-8-phenyl-octahydro-indolizin-8-yl)-4-trifluoromethyl-benzamide.

One embodiment of the invention provides compounds of formula I-B, wherein X is CH$_2$, for example 2-methoxy-6-methylsulfanyl-N-(3-phenyl-octahydro-quinolizin-3-yl)-4-trifluoromethyl-benzamide.

One embodiment of the invention provides compounds of formula I-B, wherein X is a bond, for example 2-methoxy-6-methylsulfanyl-N-(6-phenyl-octahydro-indolizin-6-yl)-4-trifluoromethyl-benzamide (diastereoisomer 1) and 2-methoxy-6-methylsulfanyl-N-(6-phenyl-octahydro-indolizin-6-yl)-4-trifluoromethyl-benzamide (diastereoisomer 2).

The present compounds of formula I and their pharmaceutically acceptable salts can be prepared by methods known in the art, for example, by processes described below, which process comprises a) reacting a compound of formula

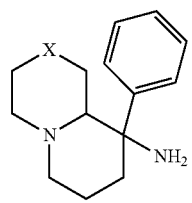

with a compound of formula

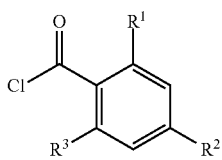

in the presence of a base like N-ethyldiisopropylamine to obtain a compound of formula

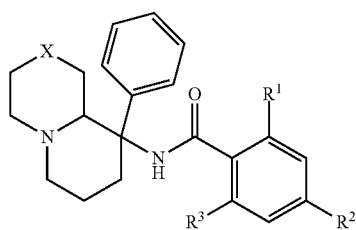

wherein the substituents are as defined above

The present compounds of formula I-B and their pharmaceutically acceptable salts can be prepared by methods known in the art, for example, by processes described below, which process comprises a) reacting a compound of formula

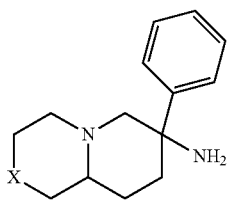

with a compound of formula

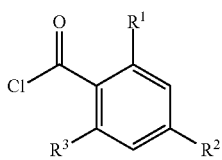

in the presence of a base like N-ethyldiisopropylamine to obtain a compound of formula

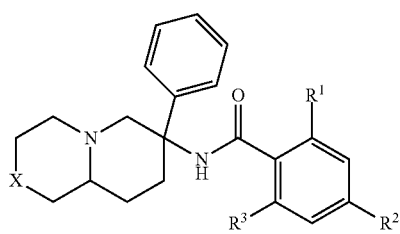

wherein the substituents are as defined above.

The compounds of formula I-A wherein X is a —$CH_2$— group can be prepared in accordance with process variant a) and with the following scheme 1. The starting material is commercially available or can be prepared in accordance with known methods.

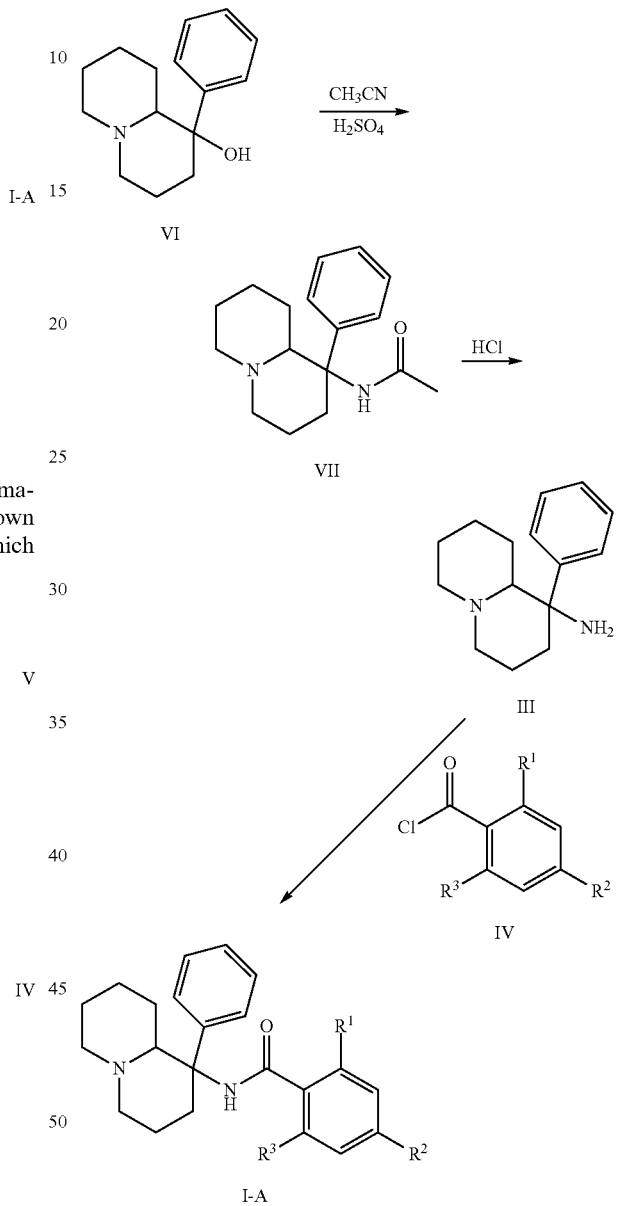

Compounds of formula I-A wherein X is a —$CH_2$— group can be prepared by reacting amino-quinazolidine derivative of formula III with acid chloride of formula IV in the presence of a base like N-ethyldiisopropylamine. Amino-quinazolidine derivative of formula III can be prepared by reacting quinolizidinol VI with acetonitrile in the presence of an acid like sulfuric acid to provide acetamide derivative VII which is transformed into III in the presence of an acid like HCl.

The compounds of formula I-A wherein X is a bond can be prepared in accordance with process variant b) and with the following scheme 2. The starting material is commercially available or can be prepared in accordance with known methods.

Scheme 2

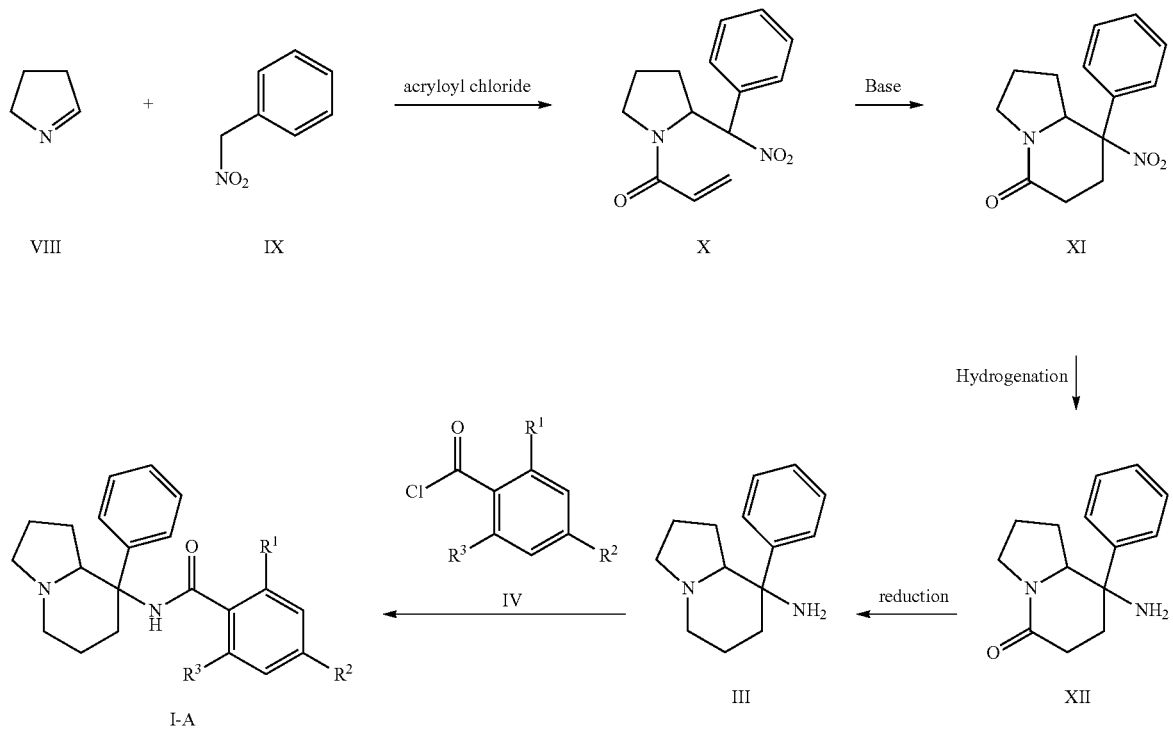

Compounds of formula I-A wherein X is a bond can be prepared by reacting amino-indolizidine derivative of formula III with acid chloride of formula IV in the presence of a base like N-ethyldiisopropylamine. Amino-indolizidine derivative of formula III can be prepared by reacting 1H-pyrroline VIII with nitro-benzyl derivative IX to provide the corresponding Mannich adduct which can be trapped in situ with acryloyl chloride to provide X which undergoes an intramolecular Michael reaction in the presence of a base such as Amberlyst A21 to provide indolizidone XI. XI can be reduced to amino-indolizidone derivative XII upon hydrogenation in the presence of a metal catalyst such as Raney-Nickel. Reaction of XII with a reducing agent such as lithium aluminium hydride provides amino-indolizidine derivative of formula III The compounds of formula I-B wherein X is a —CH$_2$— group or a bond can be prepared in accordance with process variant c) and with the following scheme 3. The starting material is commercially available or can be prepared in accordance with known methods.

Scheme 3

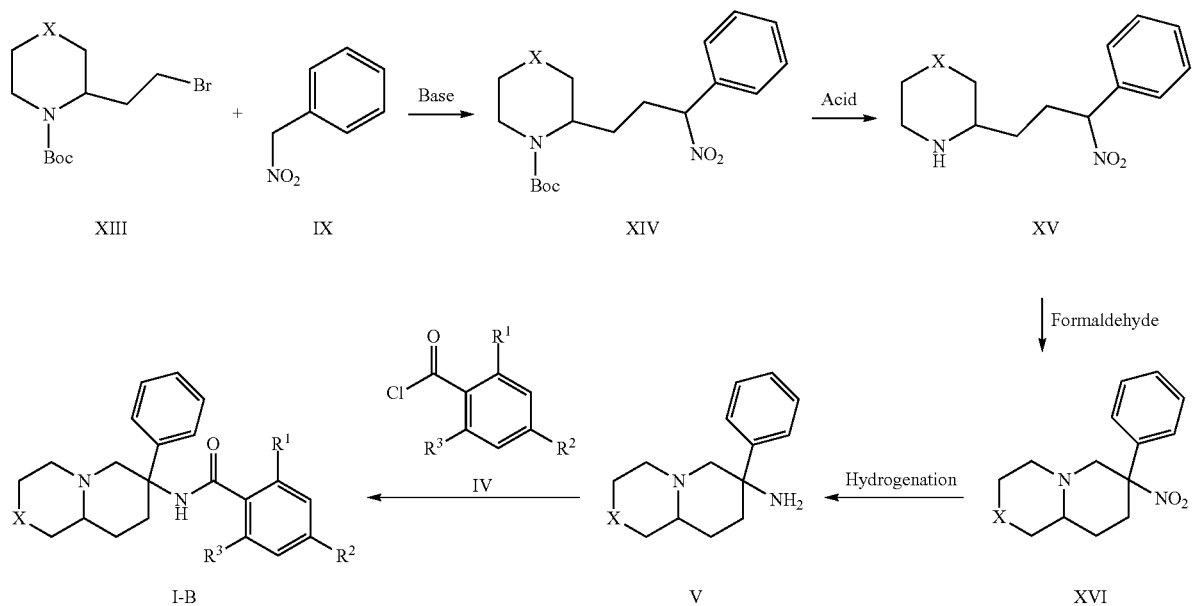

Compounds of formula I-B wherein X is a bond or a —CH₂— group can be prepared by reacting amino-indolizidine (X=bond) or quinolizidine (X=—CH₂—) derivative of formula V with acid chloride of formula IV in the presence of a base like N-ethyldiisopropylamine. V can be prepared by reacting boc-protected bromo derivative XIII with nitro-benzyl derivative IX in the presence of a base like butyl lithium to provide adduct XIV, followed by removal of the Boc-protective group in the presence of acid such as HCl, intramolecular Mannich reaction with formaldehyde and finally hydrogenation of the nitro group in the presence of a metal catalyst such as Raney-Nickel.

Racemic mixtures of chiral compound I can be separated using chiral HPLC.

The acid addition salts of the basic compounds of formula I can be converted to the corresponding free bases by treatment with at least a stoichiometric equivalent of a suitable base such as sodium or potassium hydroxide, potassium carbonate, sodium bicarbonate, ammonia, and the like.

Experimental Part

Abbreviations
HATU O-(7-azabenzotriazol-1-yl)-1,1,3,3-tetramethyluronium hexafluorophosphate
DMF Dimethylformamide
DMSO Dimethylsulfoxide
THF Tetrahydrofuran
TMEDA Tetramethylethylenediamine
Preparation of Intermediates

EXAMPLE A.1

Preparation of (1R,S; 9S,R)-1-Phenyl-octahydro-quinolizin-1-ylamine

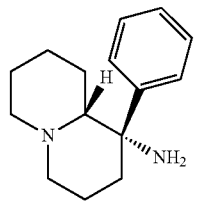

a) Step 1: N-((1R,S; 9S,R)-1-Phenyl-octahydro-quinolizin-1-yl)-acetamide

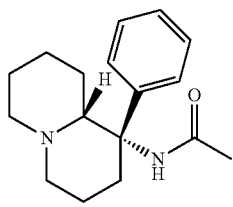

To a suspension of 710 mg (3.069 mmol) 1-phenyl-octahydro-quinolizin-1-ol (CAS: 22525-61-7) in 5.3 ml acetonitrile was added dropwise 1.8 ml sulfuric acid (98%) at 0° C. over a period of 15 minutes. The colorless solution was then stirred at room temperature for 48 hours. The solution was poured onto ice. The mixture was basified with NaOH 5N and extracted 3 times with dichloromethane. The combined extracts were dried over sodium sulfate, filtered and concentrated in vacuo. The residue was purified with flash column chromatography on silica eluting with a gradient formed from n-heptane and ethyl acetate (0 to 100%) to provide 625 mg (74.8%) of the title compound as a white solid. MS (m/e): 273.4 (M+H⁺).

b) Step 2: (1R,S; 9S,R)-1-Phenyl-octahydro-quinolizin-1-ylamine

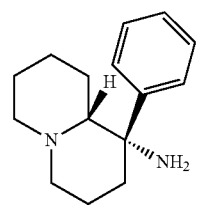

A solution of 270 mg (0.991 mmol) N-((1R,S; 9S,R)-1-phenyl-octahydro-quinolizin-1-yl)-acetamide in 5.0 ml HCl 5N was heated in a 105° C. oil bath for 6 days. The solution was cooled in an ice bath and basified with a NaOH 5N solution. The aqueous layer was extracted 6 times with dichloromethane. The combined extracts were dried over sodium sulfate, filtered and concentrated in vacuo. The residue was purified with flash column chromatography on silica eluting with a gradient formed from ethyl acetate and methanol (0 to 50%) to provide 90 mg (40%) of the title compound as a yellow solid. MS (m/e): 231.4 (M+H⁺).

EXAMPLE A.2

Preparation of (8R,S; 8aS,R)-8-Phenyl-octahydro-indolizin-8-ylamine

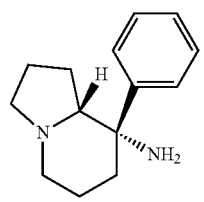

a) Step 1: (8R,S; 8aS,R)-8-Nitro-8-phenyl-hexahydro-indolizin-5-one

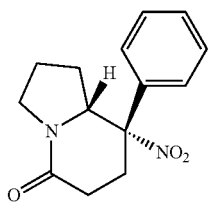

To a room temperature solution of 280 mg (2.042 mmol) nitromethyl-benzene in 3 ml dioxane was added a solution of 141 mg (2.042 mmol) 3,4-dihydro-2H-pyrrole (CAS: 638-31-3) in 0.5 ml dioxane. The mixture was stirred at room temperature for 10 min then at 60° C. for 2.5 hours then cooled to 5-10° C. and 198.2 ul (2.45 mmol) acryloyl chloride was added dropwise. The mixture was then warm to room temperature and stirred for 1 hour. The reaction mixture was quenched with saturated sodium bicarbonate and ethylacetate. The aqueous phase was extracted two times with ethylacetate. The combined organic layers were washed with brine, dried over sodium sulfate, filtered and concentrated in vacuo to provide 511 mg of light yellow oil. The crude compound was purified with flash column chromatography on silica eluting from n-heptane and ethyl acetate (0 to 40%) to provide 332 mg of an oil that was dissolved in 3 ml dioxane and 816 mg of amberlyst A-21 was added. The reaction mixture was heated to 70° C. overnight cooled to room temperature, amberlyst was filtered and washed with ethylacetate. The filtrate was concentrated in vacuo. The crude compound was purified with flash column chromatography on silica eluting from n-heptane and ethyl acetate (0 to 100%) to provide 329 mg (y: 62%) of title compound as a colorless oil. (M+H+: 261.1)

b) Step 2: (8R,S; 8aS,R)-8-Amino-8-phenyl-hexahydro-indolizin-5-one

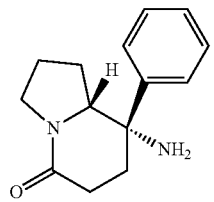

To a solution of 60 mg (0.231 mmol) (8R,S; 8aS,R)-8-nitro-8-phenyl-hexahydro-indolizin-5-one in 1 ml THF were added 100 ul of Raney Nickel (55% in water). The mixture was stirred at room temperature under a hydrogen atmosphere for 90 hours. The apparatus was purged with argon. The catalyst was filtered (under argon), washed with THF and the filtrate was concentrated in vacuo to provide 38 mg (y: 72%) of title compound as a colorless oil. (M+H+: 231.3).

c) Step 3: (8R,S; 8aS,R)-8-Phenyl-octahydro-indolizin-8-ylamine

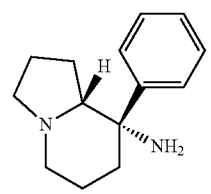

To a slurry of 14 mg (0.33 mmol) LiAlH₄ in 0.4 ml THF was added drop-wise a solution of 38 mg (0.165 mmol) (8R,S; 8aS,R)-8-amino-8-phenyl-hexahydro-indolizin-5-one in 0.4 ml THF at room temperature. The mixture was stirred at room temperature for 15 minutes and then refluxed for 30 minutes, cooled in an ice bath and quenched carefully with 15 ul water, 15 ul 5N NaOH and finally with 45 ul water. Ethyl acetate was added. The mixture was filtered and the filtrate was concentrated in vacuo to provide 30 mg (y: 84%) of the title compound as a colorless oil. (M+H+: 217.4).

EXAMPLE A.3

Preparation of 6-Phenyl-octahydro-indolizin-6-ylamine

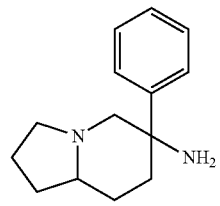

a) Step 1: 2-(3-Nitro-3-phenyl-propyl)-pyrrolidine-1-carboxylic acid tert-butyl ester

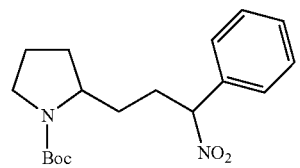

To a −78° C. solution of 200 mg (1.460 mmol) 2-(2-bromo-ethyl)-pyrrolidine-1-car boxylic acid tert-butyl ester (CAS: 958026-65-8) in 4.3 ml tetrahydrofuran over mol-sieves and 851.0 ul HMPA, was added drop-wise 1.92 ml (3.064 mmol) n-BuLi (1.6 M in hexane). After 45 minutes at −78° C., a solution of 406.2 mg (1.460 mmol) nitromethyl-benzene in 0.6 ml tetrahydrofuran over mol-sieves was added drop-wise. After 1 hour at −78° C., the reaction mixture was allowed to warm up slowly (during 5 hours) to −2° C. The mixture was then cooled again to −78° C. and quenched at this temperature with 0.4 ml of acetic acid, then with 8 ml saturated ammonium chloride. Back to room temperature, the aqueous phase was extracted 2 times with ethylacetate. The combined organic layers were washed with brine, dried over sodium sulfate, filtered and concentrated in vacuo. The crude yellow oil (993 mg) was purified with flash column chromatography on silica eluting from n-heptane and ethyl acetate (0 to 15%) to provide 242 mg (y: 49.6%) of the title compound as a colorless oil. MS (m/e): 335.2 (M+H⁺).

b) Step 2: 2-(3-Nitro-3-phenyl-propyl)-pyrrolidine

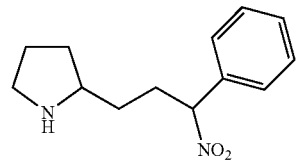

To a solution of 230 mg (0.688 mmol) 2-(3-nitro-3-phenyl-propyl)-pyrrolidine-1-carboxylic acid tert-butyl ester in 3.5 ml methanol were added 860 ul (0.3.44 mmol) of a 4M HCl solution in dioxane. The mixture was stirred at room temperature for 17 hours. The solvent was removed in vacuo. The residue was dissolved in water. The mixture was basified with a saturated sodium bicarbonate solution and extracted 6 times with dichloromethane. The combined extracts were dried over sodium sulfate, filtered and concentrated in vacuo to provide 96 mg (y: 59.6%) of the title compound as a white solid. MS (m/e): 235.2 (M+H⁺).

c) Step 3: 6-Nitro-6-phenyl-octahydro-indolizine

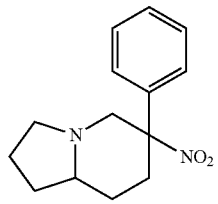

To a suspension of 95 mg (0.405 mmol) 2-(3-nitro-3-phenyl-propyl)-pyrrolidine in 1.5 ml dioxane was added 32.5 ul (0.446 mmol) formaldehyde (37% in water). The mixture was stirred at room temperature for 30 minutes to get a solution, and then heated in a 65° C. oil bath for 4 hours.

The mixture was cooled to room temperature and diluted with ethyl acetate. Sodium sulfate was added. The mixture was filtered and the filtrate was concentrated in vacuo. The residue (993 mg) was purified with flash column chromatography on silica eluting from n-heptane and ethyl acetate (0 to 10%) to provide 66 mg (y: 66.1%) of the title compound as a colorless oil. MS (m/e): 247.3 (M+H⁺).

d) Step 4: 6-Phenyl-octahydro-indolizin-6-ylamine

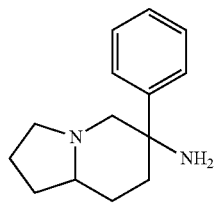

To a solution of 62 mg (0.252 mmol) 6-nitro-6-phenyl-octahydro-indolizine in 2.0 ml THF was added 150 ul Raney Nickel (50% in water). The mixture was stirred under a hydrogen atmosphere for 2 hours. The apparatus was purged with argon. The catalyst was filtered, washed with THF and the filtrate was concentrated in vacuo to provide 57 mg (y: 100%) of the title compound as a colorless oil. MS (m/e): 217.4 (M+H⁺).

EXAMPLE A.4

Preparation of 3-Phenyl-octahydro-quinolizin-3-ylamine

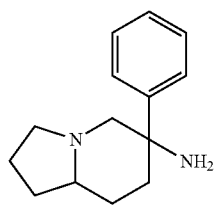

Title compound (colorless oil, MS (m/e): 231.4 (M+H⁺)), was prepared following the same sequence of reaction as described for the preparation of example A3 using 2-(2-bromo-ethyl)-piperidine-1-carboxylic acid tert-butyl ester (CAS: 210564-52-6) as starting material.

EXAMPLE B.1

Preparation of 2-Methoxy-6-methylsulfanyl-4-trifluoromethyl-benzoyl chloride

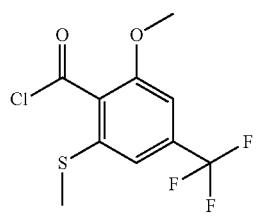

A mixture of 51 mg (0.191 mmol) 2-methoxy-6-methylsulfanyl-4-trifluoromethyl-benzoic acid (CAS 1208984-79-5) and 140 ul (1.91 mmol) thionylchloride in toluene (0.5 ml) was heated in a 80° C. oil bath for 4 hours. The solvent was removed in vacuo to provide the title compound.

Description of Active Examples:

EXAMPLE 1

2-Methoxy-6-methylsulfanyl-N-((1S,R; 9aR,S)-1-phenyl-octahydro-quinolizin-1-yl)-4-trifluoromethyl-benzamide

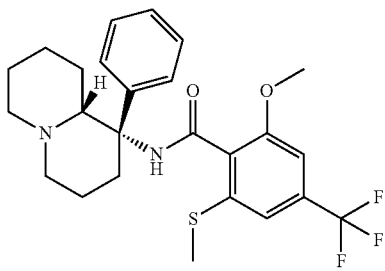

To a solution of 33 mg (0.143 mmol) (1R,S; 9S,R)-1-phenyl-octahydro-quinolizin-1-ylamine (Example A1) and 74 ul (0.429 mmol) N-ethyldiisopropylamine in dichloromethane (0.33 ml) was added drop-wise a solution of 53 mg (0.186 mmol) 2-methoxy-6-methylsulfanyl-4-trifluoromethyl-benzoyl chloride (Example B1) in dichloromethane (0.3 ml) at room temperature. The mixture was stirred at room temperature overnight. The solution was washed once with a 2M sodium bicarbonate solution. The aqueous layer was extracted once with dichloromethane. The combined organic layers were dried over sodium sulfate, filtered and concentrated in vacuo. The residue was purified with flash column chromatography on silica eluting from n-heptane and ethyl acetate (0 to 50%) to provide 44 mg (y: 64.2%) of the title compound as a light yellow oil. MS (m/e): 479.1 (M+H⁺).

EXAMPLE 2

2-Methoxy-6-methylsulfanyl-N-((8S,R; 8aR,S)-8-phenyl-octahydro-indolizin-8-yl)-4-trifluoromethyl-benzamide

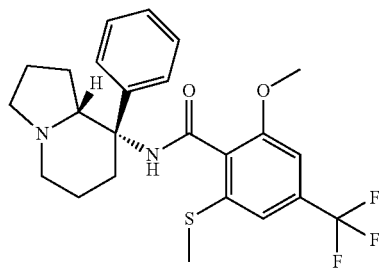

Title compound (colorless gum, MS (m/e): 465.2 (M+H$^+$)) was prepared according to the procedure described for example 1 using (8R,S; 8aS,R)-8-phenyl-octahydro-indolizin-8-ylamine (example A.2) as starting material.

EXAMPLE 3

2-Methoxy-6-methylsulfanyl-N-(6-phenyl-octahydro-indolizin-6-yl)-4-trifluoromethyl-benzamide (diastereoisomer 1)

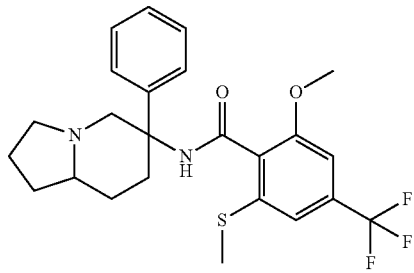

EXAMPLE 4

2-Methoxy-6-methylsulfanyl-N-(6-phenyl-octahydro-indolizin-6-yl)-4-trifluoromethyl-benzamide (diastereoisomer 2)

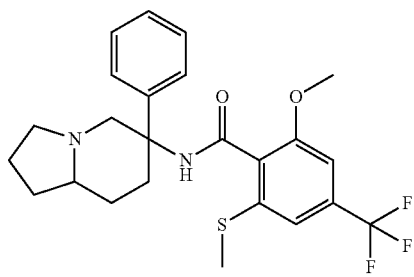

To a solution of 55 mg (0.254 mmol) 6-phenyl-octahydro-indolizin-6-ylamine (example A.3) and 130 ul (0.762 mmol) N-ethyldiisopropylamine in dichloromethane (0.9 ml) was added drop-wise a solution of 63 mg (0.22 mmol) 2-methoxy-6-methylsulfanyl-4-trifluoromethyl-benzoyl chloride (example B.1) in dichloromethane (0.6 ml) at room temperature. The mixture was stirred at room temperature for 1 hour. The solution was washed once with a 2M sodium carbonate solution. The aqueous layer was extracted once with dichloromethane. The combined organic layers were dried over sodium sulfate, filtered and concentrated in vacuo. The residue was purified with flash column chromatography on silica eluting from n-heptane and ethyl acetate (0 to 50%) to provide 26 mg (y: 22%) of example 3 (2-methoxy-6-methylsulfanyl-N-(6-phenyl-octahydro-indolizin-6-yl)-4-trifluoromethyl-benzamide, diastereoisomer 1, first running compound) as a light yellow gum, MS (m/e): 465.2 (M+H$^+$) and 49 mg (y: 41.5%) of example 4 (2-methoxy-6-methylsulfanyl-N-(6-phenyl-octahydro-indolizin-6-yl)-4-trifluoromethyl-benzamide, diastereoisomer 2, second running compound) as a white solid, MS (m/e): 465.2 (M+H$^+$).

EXAMPLE 5

2-Methoxy-6-methylsulfanyl-N-(3-phenyl-octahydro-quinolizin-3-yl)-4-trifluoromethyl-benzamide

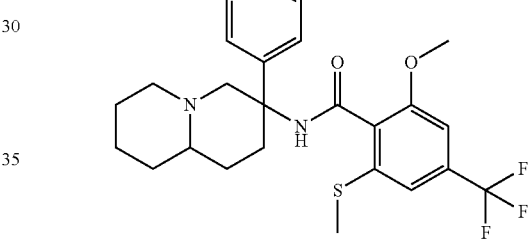

Title compound (white foam, MS (m/e): 479.1 (M+H$^+$)) was prepared according to the procedure described for example 1 using 3-phenyl-octahydro-quinolizin-3-ylamine (example A.4) as starting material.

The compounds of formula IA and I-B and their pharmaceutically usable addition salts possess valuable pharmacological properties. Specifically, the compounds of the present invention are good inhibitors of the glycine transporter I (GlyT-1). The compounds were investigated in accordance with the test given hereinafter.

Solutions and Materials

DMEM complete medium: Nutrient mixture F-12 (Gibco Life-technologies), fetal bovine serum (FBS) 5%, (Gibco life technologies), Penicillin/Streptomycinl % (Gibco life technologies), Hygromycin 0.6 mg/ml (Gibco life technologies), Glutamine 1 mM Gibco life technologies)

Uptake buffer (UB): 150 mM NaCl, 10 mM Hepes-Tris, pH 7.4, 1 mM CaCl$_2$, 2.5 mM KCl, 2.5 mM MgSO$_4$, 10 mM (+) D-glucose.

Flp-In™ CHO (Invitrogen Cat no R758-07) cells stably transfected with mGlyT1b cDNA.

Glycine uptake inhibition assay (mGlyT-1b)

On day 1 mammalian cells, (Flp-In™ CHO), transfected with mGlyT-1b cDNA, were plated at the density of 40,000 cells/well in complete F-12 medium, without hygromycin in 96-well culture plates. On day 2, the medium was aspirated and the cells were washed twice with uptake buffer (UB). The cells were then incubated for 20 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11-16 Ci/mmol) and 25 μM non-radioactive glycine. The plates were incubated with gentle shaking and the reaction was stopped by aspiration of the mixture and washing (three times) with ice-cold UB. The cells were lysed with scintillation liquid, shaken 3 hours and the radioactivity in the cells was counted using a scintillation counter.

The compounds described in examples 1-5 have an $IC_{50}$ data <0.1 μM. The $IC_{50}$ data for compounds of formula I-A and I-B are provided in table 1.

TABLE 1

| Example | $IC_{50}$ data (μM) |
|---|---|
| 1 | 0.080 |
| 2 | 0.025 |
| 3 | 0.017 |
| 4 | 0.013 |
| 5 | 0.028 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compositions containing a compound of formula I-A and I-B or a pharmaceutically acceptable salt thereof and a therapeutically inert carrier are also an object of the present invention, as is a process for their production, which comprises bringing one or more compounds of formula I-A and I-B and/or pharmaceutically acceptable acid addition salts and, if desired, one or more other therapeutically valuable substances into a galenical administration form together with one or more therapeutically inert carriers.

The most preferred indications in accordance with the present invention are those, which include disorders of the central nervous system, for example the treatment or prevention of schizophrenia, cognitive impairment and Alzheimer's disease.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I-A and I-B or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I-A or I-B | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I-A or I-B | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of formula I-A or I-B

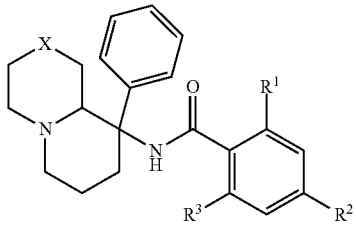   I-A

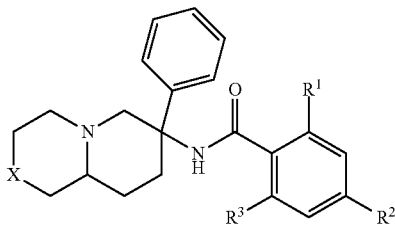   I-B wherein
X is a bond or a —CH$_2$— group;
R$^1$, R$^2$ and R$^3$ are each independently hydrogen, lower alkoxy, lower alkyl substituted by halogen or S-lower alkyl;
or a pharmaceutically acceptable acid addition salt, corresponding enantiomer or optical isomer thereof.

2. The compound of claim 1, having formula I-A, wherein X is CH$_2$.

3. The compound of claim 2, having formula I-A which is 2-methoxy-6-methylsulfanyl-N-((1S,R; 9aR,S)-1-phenyl-octahydro-quinolizin-1-yl)-4-trifluoromethyl-benzamide.

4. The compound of claim 1, having formula I-A, wherein X is a bond.

5. The compound of claim 4, having formula I-A, which is 2-methoxy-6-methylsulfanyl-N-((8S,R; 8aR,S)-8-phenyl-octahydro-indolizin-8-yl)-4-trifluoromethyl-benzamide.

6. The compound of claim 1, having formula I-B, wherein X is CH$_2$.

7. The compound of claim 6, having formula I-B, which is 2-methoxy-6-methylsulfanyl-N-(3-phenyl-octahydro-quinolizin-3-yl)-4-trifluoromethyl-benzamide.

8. The compound of claim 1, having formula I-B, wherein X is a bond.

9. The compound of claim 8, having formula I-B, wherein the compound is selected from the group consisting of
2-methoxy-6-methylsulfanyl-N-(6-phenyl-octahydro-indolizin-6-yl)-4-trifluoromethyl-benzamide (diastereoisomer 1) and
2-methoxy-6-methylsulfanyl-N-(6-phenyl-octahydro-indolizin-6-yl)-4-trifluoromethyl-benzamide (diastereoisomer 2).

10. A pharmaceutical composition comprising a compound of formula I-A or I-B

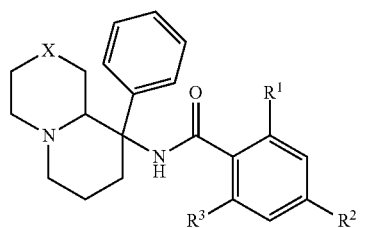   I-A

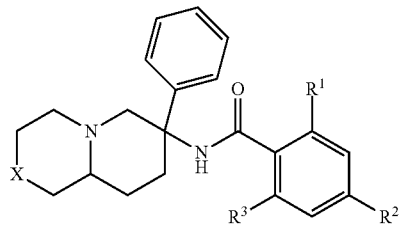   I-B wherein
X is a bond or a —CH$_2$— group;
R$^1$, R$^2$ and R$^3$ are each independently hydrogen, lower alkoxy, lower alkyl substituted by halogen or S-lower alkyl;
or a pharmaceutically acceptable acid addition salt, a racemic mixture, corresponding enantiomer and/or optical isomer thereof.

* * * * *

UNITED STATES PATENT AND TRADEMARK OFFICE
CERTIFICATE OF CORRECTION

| | | |
|---|---|---|
| PATENT NO. | : 8,143,273 B2 | Page 1 of 1 |
| APPLICATION NO. | : 13/161534 | |
| DATED | : March 27, 2012 | |
| INVENTOR(S) | : Kolczewski et al. | |

It is certified that error appears in the above-identified patent and that said Letters Patent is hereby corrected as shown below:

TITLE PAGE:

• Item "(73) Assignee: Hoffman-La Roche Inc., Nutley, NJ (US)".
should read Item -- (73) Assignee: Hoffmann-La Roche Inc., Nutley, NJ (US) --.

Signed and Sealed this
Twenty-fourth Day of July, 2012

David J. Kappos
*Director of the United States Patent and Trademark Office*